(12) United States Patent
Lackritz et al.

(10) Patent No.: US 6,787,015 B2
(45) Date of Patent: Sep. 7, 2004

(54) METHODS FOR CONDUCTING ELECTROPHORETIC ANALYSIS

(75) Inventors: Hilary Lackritz, Cupertino, CA (US); Ingrid Cruzado, San Jose, CA (US); Hongdong Tan, San Jose, CA (US)

(73) Assignee: Aclara Biosciences, Inc., Mountain View, CA (US)

( * ) Notice: Subject to any disclaimer, the term of this patent is extended or adjusted under 35 U.S.C. 154(b) by 342 days.

(21) Appl. No.: 09/911,033

(22) Filed: Jul. 20, 2001

(65) Prior Publication Data

US 2002/0056639 A1 May 16, 2002

Related U.S. Application Data

(60) Provisional application No. 60/220,059, filed on Jul. 21, 2000.

(51) Int. Cl.[7] .............................................. G01N 27/447
(52) U.S. Cl. .................. 204/451; 204/454; 204/601
(58) Field of Search .............................. 204/451, 454, 204/455, 450, 600, 601, 605

(56) References Cited

U.S. PATENT DOCUMENTS

| | | | |
|---|---|---|---|
| 6,010,608 A | * | 1/2000 | Ramsey ..................... 204/453 |
| 2002/0029968 A1 | * | 3/2002 | Tan et al. ................... 204/454 |
| 2002/0092767 A1 | * | 7/2002 | Bjornson et al. ........... 204/451 |

FOREIGN PATENT DOCUMENTS

| | | | |
|---|---|---|---|
| WO | WO 98/27423 | * | 6/1998 |
| WO | WO 02/08744 A2 | | 1/2002 |

OTHER PUBLICATIONS

Kameoka et al, Analytical Chemistry, 73(9), pp. 1935–1941, 2001.*

Ofstead, E., The Goodyear Tire & Rubber Co., et al, "Polypentenamer", Encyclopedia of Polymer Science and Engineering, 2nd Edition, vol. 11, 1988, pp. 287–315.

Eder, K. et al, "Evaluation of Norbornene–β–Cyclodextrin–Based Monomers and Ologomers as chiral selectors by Means of Nonaqueous Capillary Electrophoresis", Electrophoresis 2001, 22, pp. 1–0–116.

* cited by examiner

*Primary Examiner*—Kaj K. Olsen
(74) *Attorney, Agent, or Firm*—Stephen C. Macevicz

(57) ABSTRACT

Capillary electrophoresis is performed under conventional conditions in microchannels having a norbornene based polymer surface. The norbornene based polymers can be used as a solid substrate for forming the necessary features for a microfluidic device, where the entire device may be made of norbornene based polymer. Conveniently, a norbornene based polymer layer having a lower glass transition temperature may be used to adhere a cover or enclosing layer to the substrate to enclose the microchannels and provide a bottom for the reservoirs.

5 Claims, 6 Drawing Sheets

METHODS FOR CONDUCTING ELECTROPHORETIC ANALYSIS

This application claims the benefit of U.S. Provisional Application No. 60/220,059 filed Jul. 21, 2000, which is incorporated herewith by reference in its entirety.

FIELD OF THE INVENTION

The technical field of the invention is capillary electrophoresis.

BACKGROUND OF THE INVENTION

Capillary electrophoresis (CE) has been gaining increasing utility for conducting chemical and biochemical operations. It provides many benefits including substantial savings in time of analysis, cost of analysis, laboratory space required for performing the analysis, automation and high throughput. These benefits are due in great part to miniaturization and the alleviation of associated human factors, e.g., labor costs, costs associated with operator error, and general inconsistencies from individual to individual and overall human operation.

Due to factors such as convenience, cost and efficiency, plastic materials have become very attractive for use in the field of CE. For instance, conventional molding techniques can be used to produce large numbers of disposable plastic devices, each having precise and intricate features such as microchannel networks and reservoirs. Plastic films can also be efficiently extruded into laminates containing electrophoretic channels. Various plastics or polymers can and have been used with the molds and films mentioned above. These include polymethacrylates and other acrylics, polycarbonates, polydimethylsiloxanes, and polyalkenes, among others. The problems with each however, are complex surface chemistries accompanied with variations in wall surface charge physical and chemical configuration and microstucture. These chemistries and surface charges tend to aggravate sample adsorption to the capillary walls and generate non-uniform electroosmotic flow. Because adsorption results in skewed peaks and/or no analyte migration while non-uniform electroosmotic flow causes reduced separation resolution, reliable and consistent results have been difficult to obtain.

EOF is highly dependent upon both Zeta potential and viscosity at the vicinity of a solid micro-channel wall. The Zeta potential is the potential at the shipping plane (surface of shear) between the charged or ionized surface and the electrolyte solution or buffer, depending on the surface charge density, the buffer or medium composition and the pH. This effect is present with a variety of substrates. For example, where a conventional silica capillary is used for CE, EOF is enhanced due to the negatively charged inner walls of the capillary. These walls are dominated by silanol groups that attract a diffuse layer with excess positive ions from the electrolyte buffer. As the mobile excess positive ions in the diffuse layer flow toward the cathode under the influence of the electrical potential, the bulk solution is also dragged to the same direction.

Currently there are several ways to partially or fully control EOF and adsorption, including buffer changes and additives, use of organic solvents, adsorption of neutral and/or charged macromolecules (including surfactants) to the wall, chemically bonded phases and the like. See, for example, U.S. Pat. Nos. 4,68,201, 4,690,749, 4,865,707, 4,931,328, 5,112,460, which are incorporated herein by reference. The underlying idea is to modulate the nature of the charges on the wall to substantially reduce charged entities. Each of these methods has deficiencies and may not provide the desired reduction in EOF, while still providing other desired surface properties for the performance of CE.

SUMMARY OF THE INVENTION

Methods and devices are provided employing norbornene based polymer surfaces for performing capillary electrophoresis. Substantially saturated neutral poly (norbornene) homo- and copolymers are employed as the surface for microchannels in which ions are moved under the influence of an electric field. Improved separations and resolutions of mixtures, particularly nucleic acid mixtures, are achieved under comparable conditions using other microchannel surfaces, without the need to pretreat the surface to avoid EOF.

DESCRIPTION OF THE SPECIFIC EMBODIMENTS

Figure 1A:
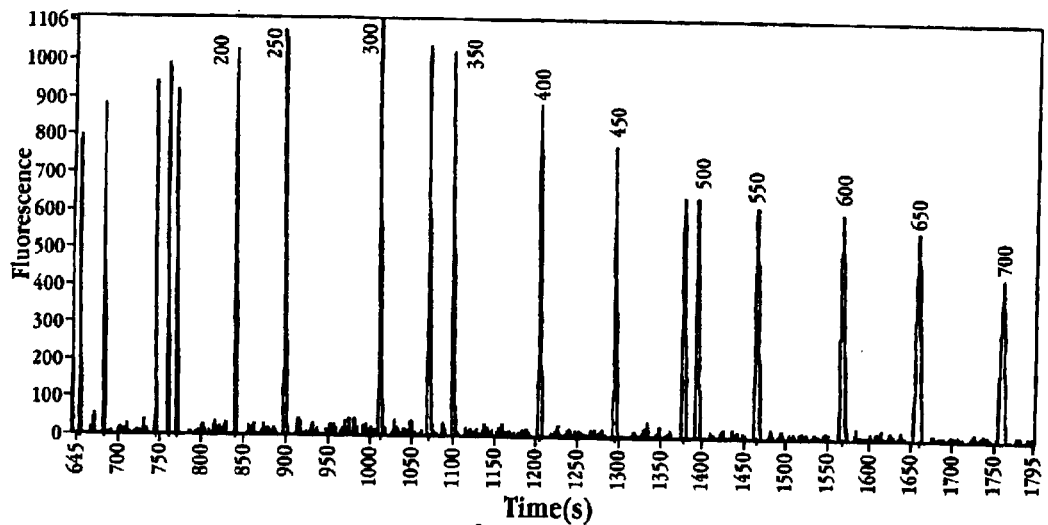
FIG. 1 is an electropherogram of a DNA separation of a DNA ladder on a bare PMMA chip and a graph of the separation intervals (crossover plot).

Methods and devices for conducting electrophoretic separations are provided employing microchannels having a neutral hydrogenated poly (norbornene) homo- or copolymer. Conveniently a substrate is employed comprising the polymer in which substrate the microchannels and other features are formed. These methods and devices allow for separations with increased resolution of analytes, particularly nucleic acid mixtures, without the need for surface modification or the addition of agents to reduce the level of EOF. The polymers can be produced using norbornene-based monomer molecules polymerized through a ring opening metathesis polymerization (ROMP) followed by hydrogenation. The polymers are substantially completely hydrocarbon, will generally have less than about 5% unsaturation (based on the number of double bonds present prior to hydrogenation), and have heat resistance, having a $T_g$ of greater than about 60° C. usually greater than about 90° C. Comonomers include substituted norbornene modified monomers, particularly alkyl substituted norbornenes and polycyclics, 1-olefins of from about 2 to 10 carbon atoms, etc.

By norbornene based polymers is intended that the polymer comprise at least about 10 mole % of a norbornene monomer, particularly where the polymer is formed by polymerization using ring opening metathesis polymerization (ROMP), followed by hydrogenation to reduce available unsaturation. Desirably, the norbornene based polymer will consist of monomers comprising norbornene and substituted norbornenes.

The norbornene monomer will usually be at least about 20 mole %, more usually at least about 50 mole %, frequently at least about 75 mole %, of the copolymers. The intrinsic viscosity of the polymers will be at least about 0.5 dl/g (as determined in toluene at 25° C.). The polymers can be prepared in conventional ways, a number of homo- and copolymers being commercially available. See, for example, U.S. Pat. No. 5,191,026. Conveniently, the polymers used for the microchannel surface or the substrate for the microchannels are produced by ring opening metathesis (ROMP) of norbornene or norbornene derivatives. The metathesis reactions are known in the art, examples of which are provided in U.S. Pat. Nos. 4,945,135; 5,198,511; 5,312,940; and 5,342,909. After polymerization, the double bonds of the main polymer chains and the substituents are substantially saturated through hydrogenation. See Hashimoto, M., Synthesis and Properties of Hydrogenated Ring Opening Metathesis Polymer, Polymeric Materials: Science and Engineering, American Chemical Society, Vol. 76, pg. 61. The subject channel surface material is amorphous, water insoluble, non-porous, nonpolar (electrically neutral) and electrically non-conductive, i.e. has a high electrical resistance. The material is stable having sufficient mechanical strength and rigidity to retain its shape under the necessary conditions for chemical operations such as those required for capillary electrophoresis, i.e. salt containing aqueous media in which the pH may range from 2 to 12. The polymers are thermoplastic and suitable for precision forming or shaping using conventional molding and extrusion processes. Web based film processing is also possible where the subject polymer is extruded into a laminate comprising the subject microchannels. See, for example, PCT/US98/21869. The films prepared will generally have a thickness in the range of about $25\mu$ to $1000\mu$ more usually in the range of about $25\mu$ to about $750\mu$.

For the most part, the subject material comprises one or more different monomers, wherein individual monomeric units along the chain may vary, depending upon whether the polymer is a homo- or copolymer, where the polymer will comprise at least about 50 mole % of monomers of the formula:

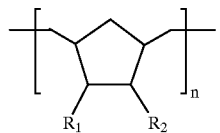

wherein $R_1$ and $R_2$ are hydrogen, alkyl of from 1 to 12, usually 1 to 6 carbon atoms or are taken together to form a ring with the carbon atoms to which they are attached, where the ring structure may be mono- or polycyclic, and will have including the carbon atoms to which they are attached, from about 5 to 12, usually from about 5 to 10 carbon atoms, and may be substituted or unsubstituted, particularly from 1 to 2 alkyl substituents of from about 1 to 6 carbon atoms.

Of particular interest are copolymers based on norbornene and, at least one of dicyclopentadiene (DCP), tetracyclododecene (TCD), 4,7-methano-2,3,3a,4,7,7a-hexahydroindene (HDCP) or dihydrodicyclopentadiene, 1,4-methano-1,4,4a,9a-tetrahydrofluorene (MTF), and the alkyl substituted derivatives thereof, particularly having from 0–2 alkyl groups of from 1 to 6, usually 1 to 3 carbon atoms.

The desired properties and overall qualities of the polymers employed for the microchannels can be manipulated through variations in the selection and ratio of the monomeric units. See Hashimoto, M., Synthesis and Properties of Hydrogenated Ring Opening Metathesis Polymer, Polymeric Materials: Science and Engineering, American Chemical Society, Vol. 76, pg. 61. For instance, in many microfluidic applications, it is desirable to have channels in a lab chip or substrate, which has a resistance to heat. Thus, the polymers will have good solvent resistance to organic solvents, light transmittance at a thickness of 3 mm (ASTM D1003) of greater than about 90% at 350 nm and above, low water absorption of <0.01 (ASTM D570); low autofluorescence, usually less than 30%, more usually less than about 20% of the lowest signal to be detected; compatible with conventional separation media, with low adsorption of the media; wettable by aqueous salt solutions under the conditions of capillary electrophoresis; and capable of molding and extrusion with retention of features that are introduced. Commercially available versions of the subject (co)polymers include the Zeonor® and Zeonex® polymer series from Nippon Zeon; the Accord® polymers from BF Goodrich; the Topas® polymers from Ticona; and the Arton® polymers from JSR. For a description of some of these polymers, see for example, Schut, J. H., New Cyclic Olefins are Clearly Worth a Look, Plastic Technology, Vol. 46, No.3, March 2000, pg. 44.

The subject microchannels of the electrophoretic devices will generally have microscale cross-sectional inner dimensions such that the independent dimensions are greater than about 1 $\mu$m and less than about 1000 $\mu$m. These independent cross sectional dimensions, i.e. width, depth or diameter depending on the particular nature of the channel, generally range from about 1 to 200 $\mu$m, usually from about 10 to 150 $\mu$m, more usually from about 20 to 100 $\mu$m with the total inner cross sectional area ranging from about 100 to 40,000 $\mu m^2$, usually from about 200 to 25,000 $\mu m^2$. The inner cross sectional shape of the channel may vary among a number of different configurations, including rectangular, square, rhombic, triangular or V-shaped, circular, semicircular, ellipsoid and the like.

The subject microfluidic devices will generally have at least two layers, where the layers may be two films, a thicker substrate and a film, a plurality of layers or laminates, where the microchannels and other features, e.g. reservoirs, may be cut, embossed, molded, etc., in one layer and the other layer(s) used to provide ports, enclose portions of the features, etc. The individual layers may be joined by heating, adhesives, thermal bonding, or other conventional means. Commonly, the devices are prepared by molding a substrate with the individual features present in the substrate and then applying a cover layer to enclose the microchannels, where access to the reservoirs may be provided in the molding process or by the cover layer.

The lab chips may have a short dimension in the range of about 0.5 to 5 cm and a long dimension in the range of about 1 to 50 cm, with one or a plurality of individual electrophoretic units, where each unit will have at least 3 reservoirs and two connecting channels. The subject channels can be serpentine, linear, branched or in some other convenient network. With a branched network it is possible to have one or more main analysis or separation channels that are intersected by one or more injection channels. With regards to main analysis or separation channels, a detection zone is usually present, generally accessible to radiation. The location of this detection zone along the length of the relevant channel depends upon the application for which the channel is being used. For example, in DNA sequencing a long electrophoretic separation channel is required to achieve proper resolution of terminal nucleotides in long DNA fragments. In such an application, the detection zone will be at or near the end of a separation channel that can be up to 18 cm in length. In other types of applications such as enzyme assays, a detection zone near the end of a long analysis channel is generally not required. For general examples of microchannels, channel networks, microfluidic chips and their operation, see U.S. Pat. Nos. 5,750,015, 5,858,188, 5,599,432 and 5,942,443 and WO96/04547, which are incorporated herein by reference.

The subject devices can be prepared in accordance with conventional ways, where the microchannel may be coated with the norbornene based polymer, although usually the norbornene based polymer will provide at least the substrate in which the features, such as the microchannels and the reservoirs are formed. The microchannels may then be enclosed and the floor of the reservoirs provided by a norbornene based polymer having the same or different composition from the substrate, adhering the enclosing layer by conventional means. The substrate can be molded or otherwise formed to have a plurality of individual microfluidic units, where each of the units may be isolated from the other units or connected The subject polymer compositions can be used in a sandwich format to prepare the microfluidic devices. A substrate may be molded, where the desired features are introduced, such as reservoirs and microchannels. The reservoir opening would extend through the substrate, while the microchannels would extend only a portion of the thickness of the substrate. A thin layer of the subject polymer composition having a lower glass transition temperature from the substrate would then be applied, followed by a third layer, that serves to enclose the microchannels and one side of the reservoirs, so that the enclosing layer need not have any structural features. Upon compression of the sandwich at or about the glass transition temperature of the middle layer, a strong adherent bond is obtained between the layers, while still preserving the nature of the microchannel surface. Generally the difference in glass transition temperature between the middle layer and the other two layers will be at least about 10° C., more usually at least about 25° C., and not more than about 50° C. As previously indicated, other techniques may also be used to fabricate the microfluidic devices.

The subject microfluidic devices do not require additives other than those used conventionally for separation. That is, in many instances, a sieving medium is used, particularly where the ions to be separated have substantially the same mass/charge ratio as is observed with nucleic acids. Even where different mass/charge ratios are involved with analytes, it is frequently desirable to have a polymeric additive in the medium in the channel to enhance separation. For the most part, the polymers will be polar and stably dispersible in aqueous media, usually soluble in aqueous media, comprising monomers including oxygen, nitrogen, etc., where the functionalities are oxy (ether and hydroxyl), non-oxo-carbonyl (ester and amide), etc.

Of particular interest is the electrophoretic separation of complex mixtures of large numbers of differently sized nucleic acids, such as DNA fragments generated for large genome sequencing applications or for single nucleotide polymorphism analysis. Of particular interest is the separation of ss or dsDNA fragments having strands ranging in size from about 10 to 10,000,000 bases, usually from about 10 to 10,000 bases, more usually from about 10 to 5,000 bases. DNA detection and sequencing methods employing microchannels are extensively described in Barron & Blach, and Lipshutz & Fodor, Curr. Opinion in Struct. Biol. (1994) 4:376–380.

For sequencing DNA, commonly the Sanger or Gilbert methods are used. These methods involve using he target DNA as a template and extending a primer in the presence of a terminating labeled nucleotide, e.g. a fluorescently labeled dideoxynucleotide. By having each of the different nucleotides differentially labeled, so that one can distinguish the different terminating nucleotides, a sequence ladder is produced that allows for the determination of the sequence. Employing the subject devices, effective and efficient separations of the individual fragments are obtained where sequences of 400 nucleotides or more, particularly at least about 500 nucleotides, can be analyzed in a single determination. This is demonstrated in FIGS. 3 and 4 with data generated from similar CE separations done on both norbornene based polymers and PMMA, the latter having been shown to be successfully used for electrophoresis. See, for example, U.S. Pat. No. 6,054,034. From this comparison, it is readily apparent that improved resolution and efficiency can be attained through the use of norbornene based polymer microchannels.

In performing chemical separations, the subject microchannels will be preloaded with separation media usually under pressure. Examples of conventional separation media include polyacrylamides, hydroxyethylcellulose (MW 50 kDa to 1000 kDa), agarose, dextran, polyethylene glycol (20 kDa to 200 kDa), poly-N-acryloyl-tris (polyNAT), poly AAEE (poly N-acryloylaminoethoxyethanol), PEO (polyethylene oxide), and the like. Appropriate buffers can also be used. See, for example, U.S. Pat. No. 5,120,413. Sample injection and use of microchannels in electrophoresis is generally described in U.S. Pat. No. 6,054,034, which is incorporated herein by reference. The standard conditions may vary according to each desired application. For electrophoresis of nucleic acids, they are generally performed with a hydrophilic separation media concentration higher than its entanglement threshold because DNA fragments with different length all have the same mass to charge ratio and the molecular sieving is the mechanism to resolve this difference. The field strength is in the range of 50–1000 V/cm, mostly between 100–200 V/cm. The temperature to perform DNA separation is in the range of 20–80C., mostly between 50 and 60 C. The common buffer systems are Tris-TAPS-EDTA, Tris-Borate-EDTA, and Sodium-TAPS buffer at pH ~8.3. For electrophoresis of small ions, hydrophilic; separation media is added into buffer at a much lower concentration, normally lower than their entanglement threshold, in order to increase the viscosity of this buffer system and prevent hydrodynamic flow within the channels. Mass to charge ratios of the small analytes still being the basis for separation. The separation field strength is between 50–2000V/cm, normally between 100 and 300 V/cm. For high-throughput screening assays, smaller molecular weight PEO polymer is added into a separation media such as 25 mM HEPES buffer. A polymer with non-ionic and hydrophilic properties is normally preferred in this case but is not always necessary.

The subject devices employing the norbornene based polymers provide for excellent separation performance. The subject devices provide for enhanced separations of sample components, finding particular application in DNA sequencing using conventional separation media, allowing for improved separations over a broader range of fragment sizes.

The following examples are offered by way of illustration and not by way of limitation.

EXPERIMENTAL

Nucleic Acid Sequencing

Chip layout

Figure 5A:
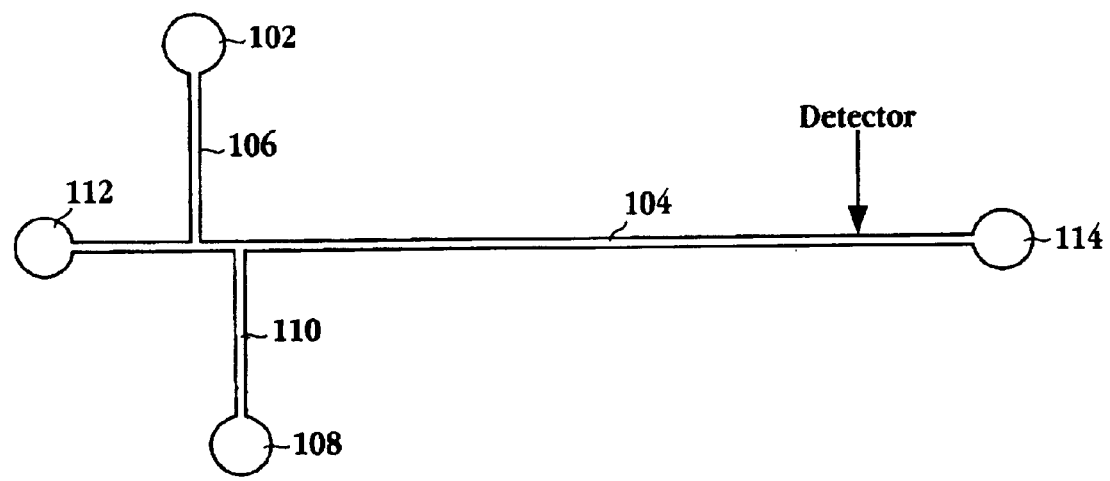
FIG. 5 is a diagrammatic view of a microfluidic pattern.
FIG. 5b is a cross-section of a channel.
Figure 5B:

The plastic microchips used in this experiment were produced by hot embossing with a nickel electroform master containing the desired electrophoresis pattern. The electrophoresis device includes a double tee injector and a main separation microchannel as illustrated in FIG. 5. The device 100 is depicted diagrammatically by lines indicating channels and circles indicating reservoirs. The sample reservoir is connected to the analytical channel 104 by side channel 106, while the sample waste reservoir is connected to the analytical channel 104 by second side channel 110. The sample reservoir 102 and waste reservoir 108 with their associated side channels 106 and 110 serve to inject the sample into the analytical channel 104. The double tee injector had a gap of 250 $\mu$m that intersected with the analytical channel 104. Buffer reservoir 112 and waste reservoir are at opposite ends of the analytical channel 104. The analytical channel 104 cross-section is depicted in FIG. 5b. The distance from the center of the injector to the detection point was about 18 cm. The four accessing reservoirs containing buffer 112, sample waste buffer 108, waste buffer 114 and sample 102 were about 1.5 mm in diameter. Other than the waste reservoir 114, the other reservoirs were 4 mm from the double tee injection intersection. Electrodes, not shown, were placed in each of the reservoirs for automatic control of the field strength. The plastic microchips were made of poly(methylmethacrylate) (PMMA) or Zeonor 1420R (Nippon Zeon Co., Ltd., Kawasaki, Japan). The poly(methyl methacrylate) microchips are prepared from materials used in house and found to provide good separations when appropriate surface modification or additives are employed. (see, McCormick, et al., Anal. Chem. 1997, 69, 2626–2630, from the laboratory of the assignee of the subject invention; and Soper, et al., Journal of Chromatography A, 833 (1999) 107–120.)

Preparation of LPA separation media

The polymerization was performed according to the protocol described in Eur. Polym. J. 1984, 20, 505–512 with slight variations. In a Pyrex reaction flask, a 40% w/w solution of acrylamide was dispersed in a solution of 2.4% SPAN 80 in petroleum special to a volume ratio of 1:1. APDS and TEMED were used to catalyze the reaction, both at a final concentration of 0.0055 w/v. To remove oxygen, the entire dispersion was purged continually with nitrogen, and then the polymerization reaction was performed at 350° C. overnight. Acetone was used to precipitate the polyacrylamide. The precipitate was washed several times with acetone on a Buechner funnel, and residual solvent was removed under oil-pump vacuum on a rotary evaporator. To prepare 2% LPA matrix solution for DNA sequencing, the dry polymer, urea, buffer concentrate, and water were added to the desired concentrations in a glass jar and then slowly stirred with a magnetic bar.

Preparation of LDD30 hydrophobic copolymer

The LDD30 polymer is a non-crosslinked polymer synthesized by free-radical solution polymerization. The polymerization is carried out in an aqueous solution of the monomers, diethylacrylamide and dimethylacrylamide (70:30). The total concentration of monomers is about 10% or less (w/v). The solution is de-gassed before synthesis by bubbling argon, helium, or nitrogen. Polymerization is initiated by addition of ammonium persulfate and TEMED (tetramethylethylenediamine). This solution is subjected to dialysis against purified water and freeze-drying to remove unreacted monomer and to obtain the polymer in solid form.

LDD30 is a composition defined as 30% diethylacrylamide, 70% dimethylacrylamide by weight, where the percentages are expressed as a percent of the total mass of monomers in the solution before polymerization. This composition has been found to have desirable separation and coating properties. Polymers with other ratios of the two monomers can be useful, depending upon the performance requirements. The extent of incorporation of each monomer into the resulting polymer has not been assayed.

GeneScan 700 DNA ladder

GeneScan 700 DNA ladder is a set of specially engineered DNA fragments labeled with a fluorescent dye (TET, 6-carboxy-4,7,2',b 7'-tetrachlorofluoroseein, emission wavelength: 540 nm; excitation wavelength: 520 nm). GeneScan 700 contains 20 fragments including 35 bp, 50 bp, 75 bp, 100 bp, 139 bp, 150 bp, 160 bp, 200 bp, 250 bp, 300 bp, 340 bp, 350 bp, 400 bp, 450 bp, 490 bp, 500 bp, 550 bp, 600 bp, 650 bp, and 700 bp. Under the experimental condition used, only 18 fragments were observed which excludes 35 bp and 50 bp due to the interference of small fluorescent fragments co-migrating in this region. The loading sample was prepared with 5$\mu$ GeneScan 700, 5 $\mu$l deionized water, and 10 $\mu$L deionized formamide. The loading sample was then denatured at 95° C. for 2 minutes before chilling in an ice bath.

Separation conditions

LPA, the hydrophilic separation medium referenced above, was loaded from buffer waste reservoir (114) by applying 150 to 200 psi for 2 to 5 minutes. After being loaded with sample and buffer in the remaining reservoirs, as appropriate, the whole microchip was placed on a thermal station and heated to 35° C. A Peltier device thermally controlled the thermal station. Conventional fluorescence detection was employed. The data acquisition rate was about 10 Hz while a 488 nm Ar ion laser was used with a laser power of about 7 mW. The separation field strength was about 150 V/cm. The voltage setup is listed in the following table:

| Notation Name | 1<br>Buffer Well 112 | 2<br>Sample 102 | 3<br>Buffer Waste 114 | 4<br>Sample Waste 108 | Time (s) |
|---|---|---|---|---|---|
| pull through | 0 | 0 | 0 | 500 | 90 |
| relaxation | 0 | 0 | 0 | 100 | 20 |
| separation | 0 | 310 | 3020 | 300 | 10000 |

Crossover Plot for data analysis

Crossover plots of peak interval and peak width were plotted against DNA fragment size. These plots are provided in FIGS. 1 and 2. The peak interval is the spatial distance between two DNA fragments differing by one nucleotide in length. The peak width refers to the full width at half peak height maximum (FWHM). The point where the two lines cross over indicates the single base resolution limit of the separation and corresponds to a resolution value of 0.59. The peak widths were measured using the Blue channels at wavelength 515–530 nm. The peak widths were fitted to a second-order polynomial. The data was base-lined and analyzed with crossover tool software from PE Biosystems.

Comparison was also made using glass chips, where a coating polymer, LDD30 was employed. Glass does not provide a useful separation in the absence of a coating polymer. The separation was performed at 40° C. with an effective separation field strength of 150V/cm.

REPRESENTATIVE DATA

DNA separation on PMMA chip

Figure 1B:
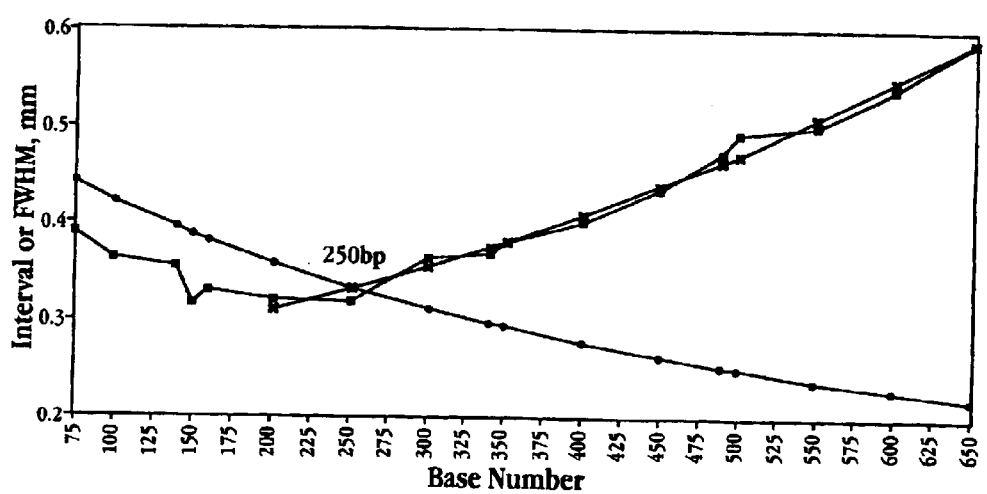

DNA separation was done on sandwich chips prepared in house (See, for example, Song, et al., Electrophoresis 1999, 20:2847–2855 for a description of the use of PMMA as a material for microfluidic devices using a nonionic surfactant coating.) with 150V/cm and 35° C., 2% high molecular weight LPA in 1×TTE (1×TTE=50 mM Tris; 50 mM TAPS; and 2 mM EDTA, pH 8.2) and 7M urea solution was used in separating GeneScan 700 DNA ladders. Many consecutive runs were performed. Regardless of how the channel surfaces were treated and cleaned, the crossover point was never higher than 300 bases. FIG. 1 shows the separation of GeneScan 700 ladder on the sandwich chips and the relevant crossover plot. In this case, the crossover point is 250 bp. This suggests that the residual EOF from PMMA surface, although the viscosity of the sieving matrix is high, is relatively high and can cause the decline of the resolution of DNA separation. This is in accordance with the fact that in various studies, adequate resolution (close to 500 bp) cannot be achieved without using nonconventional separation polymers or surface pretreatment.

DNA separation on Zeonor chip

Figure 2A:
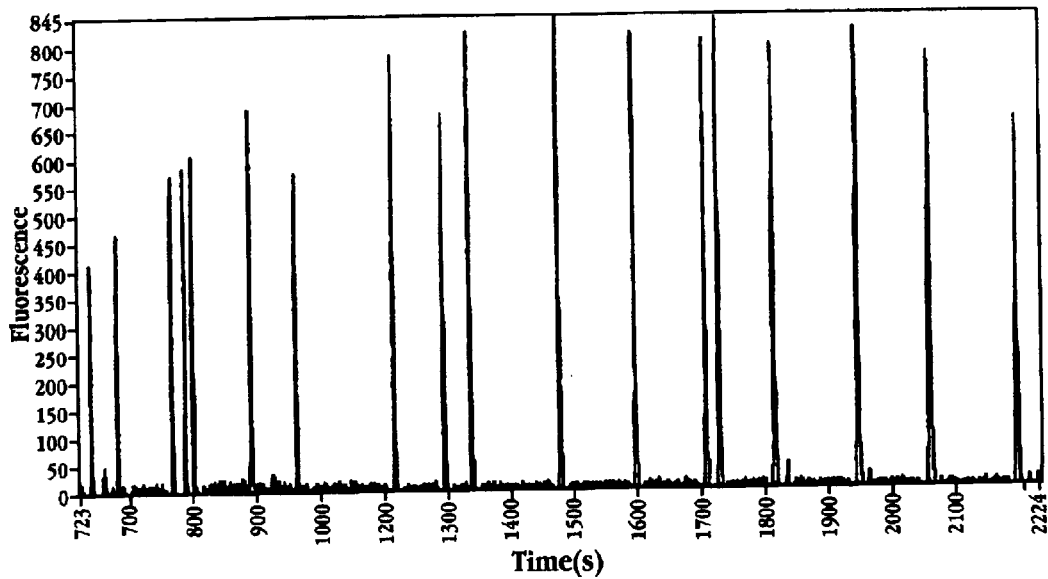
FIG. 2 is an electropherogram of a DNA separation of a DNA ladder on a bare norbornene based polymer chip and a graph of the separation intervals (crossover plot).
Figure 2B:
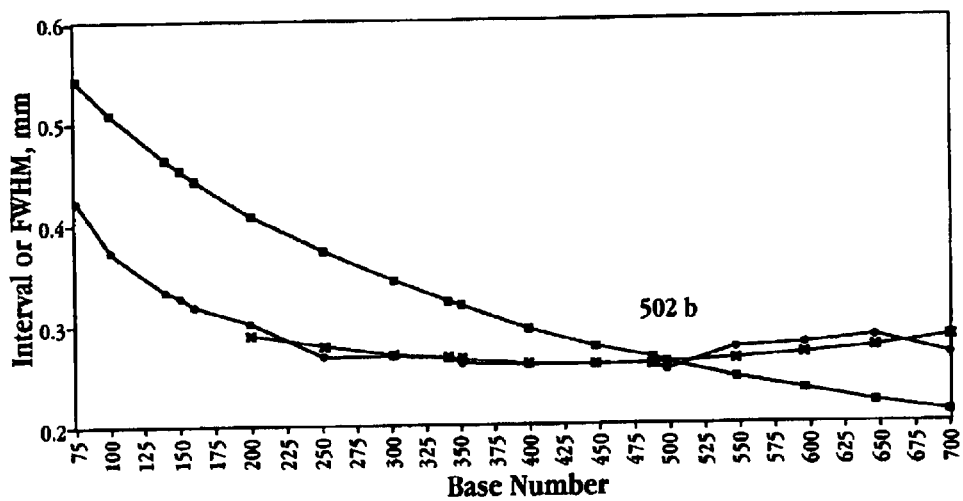
Figure 3A:
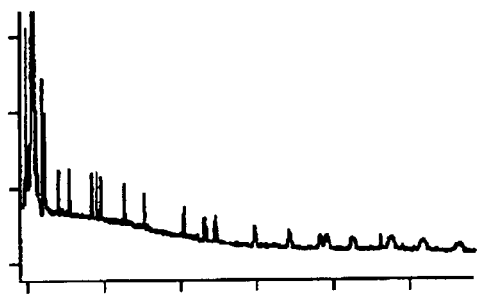
FIG. 3 shows the results from the initial consecutive DNA separations of a DNA ladder conducted on a PMMA chip using 2.4% LPA, 1×TTE and 7M urea.
Figure 3B:
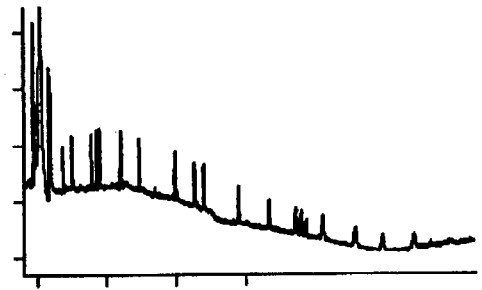
Figure 3C:
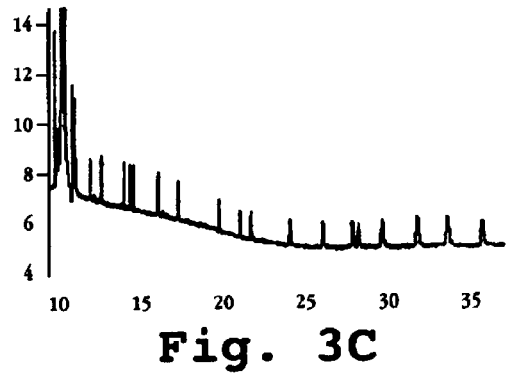
Figure 3D:
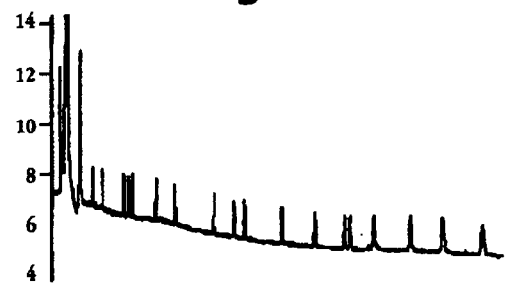
Figure 4A:
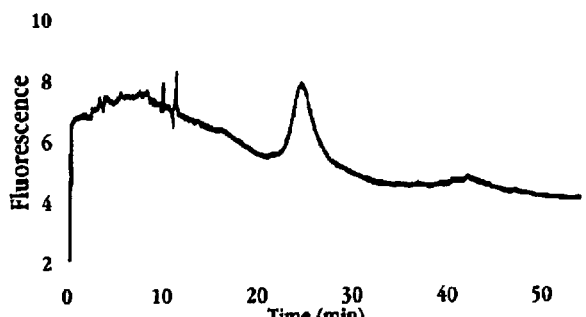
FIG. 4 shows the results from the initial consecutive DNA separations of a DNA ladder conducted on a norbornene based polymer chip using 2.4% LPA, 1×TTE and 7M urea.
Figure 4B:
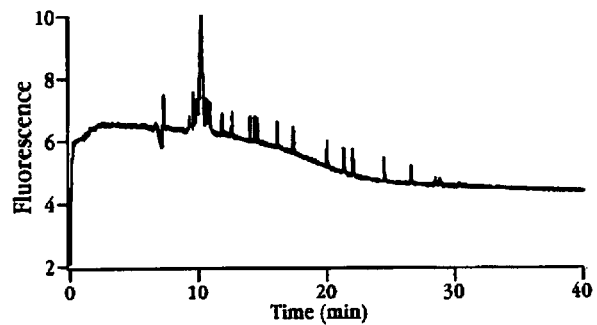
Figure 4C:
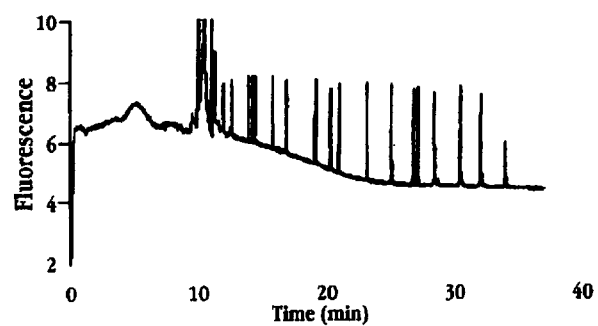
Figure 4D:
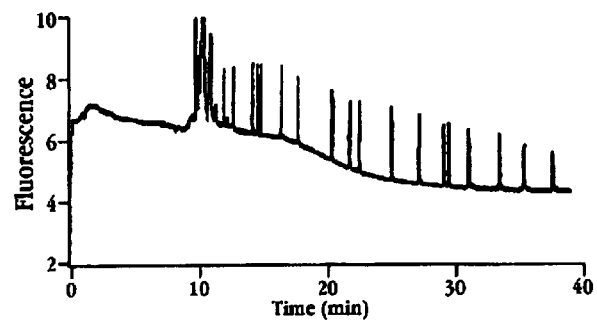

The separation of the same sample (GeneScan 700 ladder labeled with TET) was carried out on a Zeonor sandwich chip made of Z1420R/Z1020R/Z1420R combination, where the layers were thermally compressed, the Z1020R composition having a lower glass transition temperature, so as to serve as the adhering layer. The two outer layers were 1 mm thick with the intermediate layer having a thickness in the range of 50–100 μm. One of the outer layers was embossed with the channel pattern using a master to imprint the pattern on the layer. The same 2% LPA solution in 1×TTE and 7M urea was used as sieving matrix and the experiment was conducted under 35° C. and 150V/cm. The results are shown in FIG. 2. After several runs with the same sieving matrix flushing, the separation of GeneScan 700 reached a resolution of up to 525 bp in reference to the crossover point. FIG. 4 shows several electrophoregrams for DNA separation of GeneScan 700 on Zeonor sandwich chips. From these graphs, it is apparent that the bare Zeonor surface can provide DNA separation up to 500 bp without any modification.

The following table is a comparison of consecutive runs of DNA separation on the two different surfaces of PMMA and Zeonor. It suggests that the Zeonor surface can provide the interaction with 2% LPA solution so that it will reduce the EOF, but the PMMA does not.

| Run # | Crossover Point on Zeonor | Crossover Point on PMMA |
|---|---|---|
| 1 | none | 275 |
| 2 | none | 300 |
| 3 | 463 | 250 |
| 4 | 489 | 260 |
| 5 | 525 | 266 |

Figure 6:
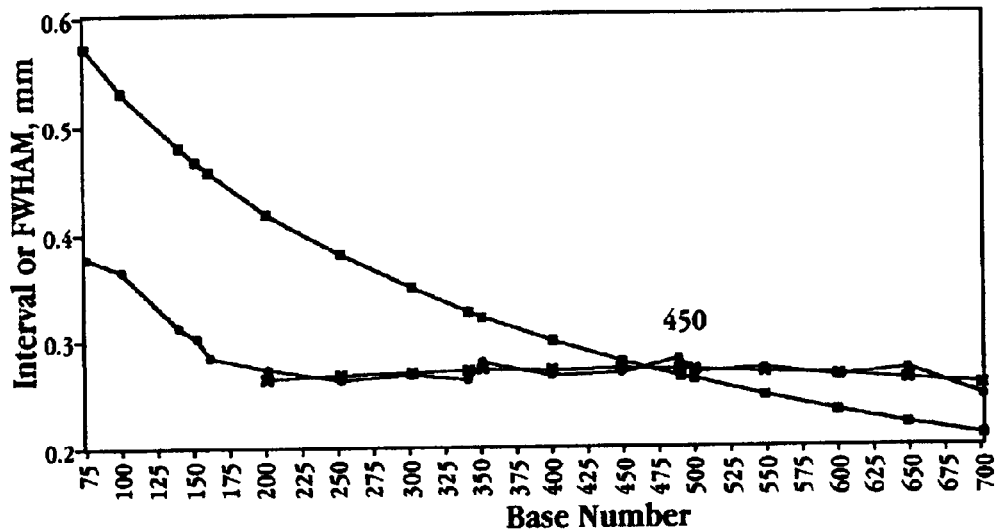
FIG. 6 is a crossover plot for separation of a DNA ladder on a glass microchip using a coating composition.
Figure 7:
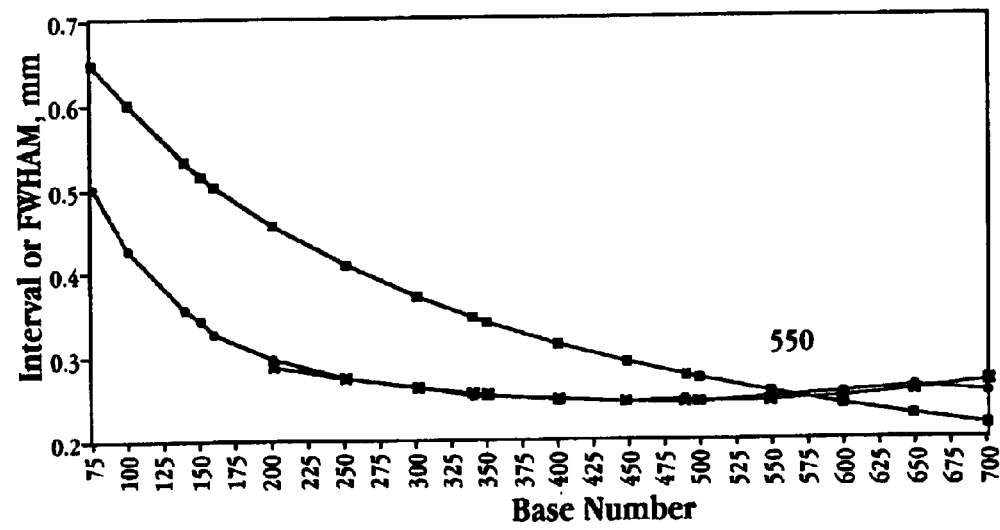
FIG. 7 is a crossover plot for separation of a DNA ladder on a norbornene based polymer microchip using the same coating composition as used for the glass microchip.

FIGS. 6–7 respectively depict crossover plots of the results with glass chips and norbornene based polymer chips, showing that in the presence of the same surface coating material, the norbornene based polymer chip is substantially better in separation than the glass chip and the surface coating does provide a small separation enhancement with the norbornene based polymer chip as compared to the absence of the coating composition.

It is evident from the above results and discussion that the polymeric microchannels according to the subject invention provide excellent performance in the electrophoretic separation of ions. The surfaces do not require prior treatment and the system is operative in the presence of conventional sieving media. No special additives or treatment of the surface is required.

All publications, patents and patent applications mentioned in this specification are herein incorporated by reference to the same extent as if each individual publication, patent, or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for separating a mixture of ions in a sample employing a microfluidic device comprising a microchannel having a neutral substantially saturated norbornene based polymer surface and two electrodes for creating an electrical field in said microchannel, said method comprising:

introducing said sample into said microchannel comprising an aqueous dispersion of a sieving polymer under the electrical influence of said field, whereby ions in said sample migrate in said aqueous dispersion to separate into fractions.

2. A method according to claim 1, wherein said ions are nucleic acid ions.

3. A method according to claim 1, wherein said sieving polymer is an acrylamide.

4. A method according to claim 1, wherein said norbornene based polymer is a hydrocarbon copolymer.

5. A method according to claim 4, wherein said hydrocarbon copolymer is a copolymer of norbornene derivatives.

* * * * *